United States Patent [19]

Drabek

[11] Patent Number: 5,132,325
[45] Date of Patent: Jul. 21, 1992

[54] BENZOYLPHENYLUREAS THE PREPARATION THEREOF AND THE USE THEREOF IN PEST CONTROL

[75] Inventor: Jozef Drabek, Oberwil, Switzerland

[73] Assignee: Ciba-Geigy Corporation, Ardsley, N.Y.

[21] Appl. No.: 656,108

[22] Filed: Feb. 13, 1991

Related U.S. Application Data

[63] Continuation of Ser. No. 240,891, Sep. 6, 1988, abandoned, which is a continuation of Ser. No. 18,879, Feb. 25, 1987, abandoned.

[30] Foreign Application Priority Data

Feb. 28, 1986 [CH] Switzerland ............... 808/86
Nov. 19, 1986 [CH] Switzerland ............... 4617/86
Dec. 24, 1986 [CH] Switzerland ............... 5238/86

[51] Int. Cl.$^5$ .................... A01N 47/34; C07C 275/54
[52] U.S. Cl. ........................................ 514/594; 564/44
[58] Field of Search ......................... 564/44; 514/594

[56] References Cited

U.S. PATENT DOCUMENTS

| 4,533,676 | 8/1985 | Sirrenberg et al. ............. 514/535 |
| 4,632,938 | 12/1986 | Nagase et al. ................... 564/44 |
| 4,798,837 | 1/1989 | Drabek et al. .................. 514/594 |

FOREIGN PATENT DOCUMENTS

| 0142667 | 5/1985 | European Pat. Off. ............ 514/594 |
| 0226642 | 12/1986 | European Pat. Off. ............ 514/594 |
| 60-246349 | 12/1985 | Japan .................................. 564/44 |
| 2166134 | 4/1986 | United Kingdom ................. 514/594 |

*Primary Examiner*—Richard L. Raymond
*Attorney, Agent, or Firm*—Edward McC. Roberts

[57] ABSTRACT

The invention relates to novel substituted N-benzoyl-N'-2,5-dihalo-4-haloalkoxyphenylureas of formula I

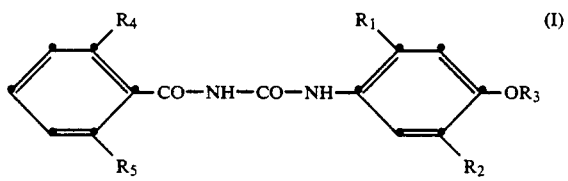

wherein each of $R_1$ and $R_2$ is halogen, with the proviso that $R_1$ and $R_2$ may not simultaneously be chlorine, $R_3$ is a mono- or polyhalogenated $C_1$-$C_7$alkyl group, $R_4$ is hydrogen, halogen, methyl, methoxy or methylthio and $R_5$ is halogen, methyl, methoxy or methylthio, to processes and intermediates for the preparation thereof, to the use thereof in pest control and to compositions containing, as active ingredient, at least one compound of formula I. The preferred area of application of said novel compounds is the control of pests of animals and plants.

7 Claims, No Drawings

BENZOYLPHENYLUREAS THE PREPARATION THEREOF AND THE USE THEREOF IN PEST CONTROL

This application is a continuation of application Ser. No. 240,891, filed Sep. 6, 1988, now abandoned, which is a continuation of application Ser. No. 018,879 filed on Feb. 25, 1987, now abandoned.

The present invention relates to novel substituted N-benzoyl-N'-2,5-dihalo-4-haloalkoxyphenylureas, to processes and intermediates for the preparation thereof, and to the use thereof in pest control.

The compounds of this invention are of formula I

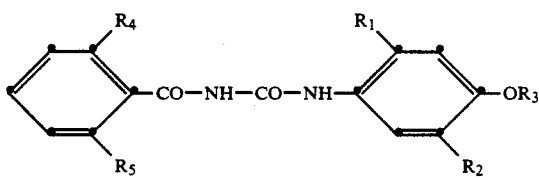

wherein each of $R_1$ and $R_2$ is halogen, with the proviso that $R_1$ and $R_2$ may not simultaneously be chlorine, $R_3$ is a mono- or polyhalogenated $C_1$-$C_7$alkyl group, $R_4$ is hydrogen, halogen, methyl, methoxy or methylthio and $R_5$ is halogen, methyl, methoxy or methylthio.

Suitable halogen substituents are fluorine, chlorine, bromine and iodine, with fluorine, chlorine and bromine being preferred.

The mono- or polyhalogenated $C_1$-$C_7$alkyl groups suitable as substituents may be straight chain or branched and may be only partially halogenated or may be perhalogenated, with halogen in said substituents being as defined above. Particularly suitable examples of such substituents are, inter alia, methyl substituted by 1 to 3 fluorine, chlorine and/or bromine atoms, e.g. $CHF_2$ or $CF_3$; ethyl substituted by 1 to 5 fluorine, chlorine and/or bromine atoms, e.g. $CH_2CF_3$, $CF_2CF_3$, $CF_2CCl_3$, $CF_2CHCl_2$, $CF_2CHF_2$, $CF_2CHBr_2$, $CF_2CHClF$, $CF_2CHBrF$ or $CClFCHClF$; propyl or isopropyl, each substituted by 1 to 7 fluorine, chlorine and/or bromine atoms, e.g. $CH_2CHBrCH_2Br$, $CF_2CHFCF_3$, $CH_2CF_2CF_3$ or $CH(CF_3)_2$; butyl substituted by 1 to 9 fluorine, chlorine and/or bromine atoms, or an isomer thereof, e.g. $CF(CF_3)CHFCF_3$ or $CH_2(CF_2)_2CF_3$.

Particularly interesting compounds of formula I are those wherein each of $R_1$ and $R_2$ is fluorine, chlorine or bromine, with the proviso that $R_1$ and $R_2$ may not simultaneously be chlorine, $R_3$ is a mono- or polyhalogenated $C_1$-$C_4$alkyl group, $R_4$ is hydrogen, fluorine or chlorine and $R_5$ is fluorine, chlorine or methoxy.

Preferred compounds of formula I are those wherein $R_1$ is fluorine and $R_2$ is fluorine, chlorine or bromine or $R_1$ is chlorine and $R_2$ is fluorine, $R_3$ is a $C_1$-$C_3$alkyl group substituted by 1 to 7 halogen atoms, $R_4$ is hydrogen, fluorine or chlorine and $R_5$ is fluorine, chlorine or methoxy.

Compounds of formula I meriting particular mention are those wherein $R_1$ is fluorine and $R_2$ is fluorine, chlorine or bromine, $R_3$ is the radical $CH_2CF_3$, $CClFCHClF$, $CF_2CHBr_2$, $CH(CF_3)_2$, $CH_2CF_2CF_3$ or $CF_2CHFCF_3$, $R_4$ is hydrogen or fluorine and $R_5$ is fluorine, chlorine or methoxy.

Compounds of formula I to be singled out for more particular mention are those wherein $R_1$ is fluorine and $R_2$ is fluorine, chlorine or bromine, $R_3$ is the radical $CH_2CF_3$, $CH(CF_3)_2$, $CH_2CF_2CF_3$ or $CF_2CHFCF_3$, $R_4$ is hydrogen or fluorine and $R_5$ is fluorine, chlorine or methoxy.

Examples of compounds of formula I are, inter alia:

| $R_1$ | $R_2$ | $R_3$ | $R_4$ | $R_5$ |
|---|---|---|---|---|
| F | Cl | $CF_2CHFCF_3$ | F | F |
| F | Cl | $CF_2CHClF$ | F | F |
| F | Cl | $CClFCHClF$ | F | F |
| F | Cl | $CH_2CF_2CF_3$ | F | F |
| F | Cl | $CF_2CHFCF_3$ | $SCH_3$ | F |
| F | F | $CF_2CCl_3$ | H | $OCH_3$ |
| F | F | $CH(CF_3)_2$ | $CH_3$ | $CH_3$ |
| F | F | $CH_2CF_3$ | Br | Br |
| F | Br | $CF_2CF_3$ | F | F |
| F | Br | $CCl_3$ | Cl | $SCH_3$ |
| F | Br | $CHF_2$ | H | F |
| Cl | Br | $CHBr_2$ | H | $OCH_3$ |
| Cl | Br | $CF_2CHF_2$ | H | Cl |
| Cl | Br | $CF_2CHF_2$ | F | F |
| Cl | F | $CF_2CHBr_2$ | F | Cl |
| Cl | F | $CF_2CHFCF_3$ | $OCH_3$ | $OCH_3$ |
| Cl | F | $CF_2CF_2CF_3$ | H | $OCH_3$ |
| Br | F | $CH_2CF_2CF_3$ | F | $SCH_3$ |
| Br | F | $CF_2(CF_2)_5CF_3$ | Cl | $SCH_3$ |
| Br | F | $CF_2(CHF)_3CF_3$ | $SCH_3$ | $SCH_3$ |
| Br | Br | $CH_2C(CF_3)_2CF_3$ | $CH_3$ | $OCH_3$ |
| Br | Br | $CF_2(CHF)_3CF_3$ | $CH_3$ | F |
| Br | Br | $CF_2(CHF)_4CF_3$ | H | Cl |
| Br | Cl | $CF_2CH(CF_3)_2$ | H | F |
| Br | Cl | $CH(CF_3)_2$ | F | F |
| Br | Cl | $CH_2CF_3$ | F | Cl |

The compounds of this invention can be prepared by processes which are known per se. Such processes are described, inter alia, in German Offenlegungsschrift specifications 21 23 236, 26 01 780 and 32 40 975. Thus the compounds of formula I can be obtained e.g. by reacting a) an aniline of formula II

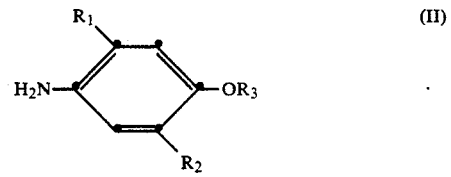

with a benzoylisocyanate of formula III

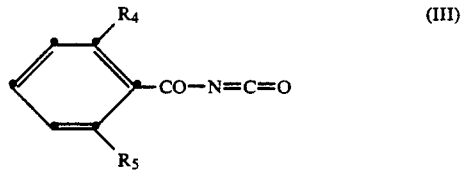

or b) an isocyanate of formula IV

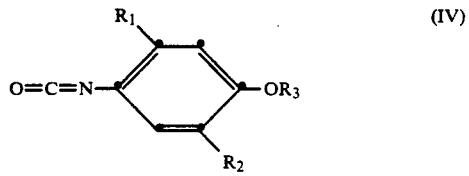

with a benzamide of formula V

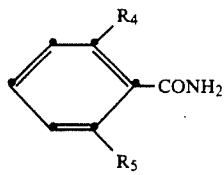

or c) an aniline of formula II with a urethane of formula VI

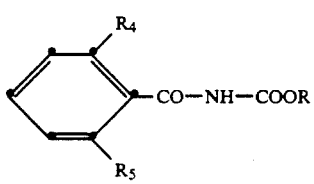

in which formula II to VI above the radicals $R_1$, $R_2$, $R_3$, $R_4$ and $R_5$ are as defined for formula I and R is a $C_1$-$C_8$alkyl radical which may be substituted by halogen, preferably chlorine.

The above processes a), b) and c) can preferably be carried out under normal pressure and in the presence of an organic solvent or diluent. Examples of suitable solvents or diluents are: ethers and ethereal compounds, such as diethyl ether, dipropyl ether, dibutyl ether, dioxane, dimethoxyethane and tetrahydrofuran; N,N-dialkylated carboxamides; aliphatic, aromatic and halogenated hydrocarbons, especially benzene, toluene, xylene, chloroform, methylene chloride, carbon tetrachloride and chlorobenzene; nitriles such as acetonitrile or propionitrile; dimethyl sulfoxide; and ketones, e.g. acetone, methyl ethyl ketone, methyl isopropyl ketone and methyl isobutyl ketone. Process a) is normally carried out in the temperature range from $-10°$ to $+200°$ C., preferably from $0°$ to $100°$ C., e.g. at room temperature, and, if desired in the presence of an organic base, e.g. triethylamine. Process b) is carried out in the temperature range from $0°$ to $150°$ C., preferably at the boiling point of the solvent employed and, if desired, in the presence of an organic base such as pyridine, and/or with the addition of an alkali metal or alkaline earth metal, preferably sodium. For process c), i.e. for the reaction of the urethane of formula VI with an aniline of formula II, a temperature range from about $60°$ C. to the boiling point of the reaction mixture is preferred, and the solvent employed is preferably an aromatic hydrocarbon such as toluene, xylene, chlorobenzene and the like.

The starting materials of formulae III and V are known and can be prepared by methods analogous to known ones.

The starting materials of formula II are novel compounds which likewise constitute an object of the present invention. The compounds of formula II can be prepared in a manner known per se by hydrogenating suitably substituted nitrobenzenes of formula VII

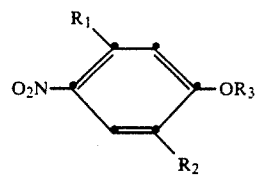

by a process analagous to that described in J. Org. Chem. 29 (1964), 1, (q.v. also the literature cited therein). However, the anilines of formula II can also be obtained by chemical reduction (e.g. with Sn(II) chloride/HCl) of the corresponding nitro compounds of formula VII (q.v. Houben-Weyl, "Methoden d. org. Chemie" 11/1, 422). A further process for the preparation of the anilines of formula II comprises haloalkylating a non-acylated or acylated 2,5-dihalo-4-hydroxyaniline and then, if appropriate, removing the acyl group, e.g. by acid hydrolysis.

The nitro compounds of formula VII are also novel and constitute an object of the present invention. They can be prepared e.g. by haloalkylating a 2,5-dihalo-4-nitrophenol (q.v. French patent specification 2,005,876) or by reacting 2,5-dihalo-4-fluoronitrobenzene with a haloalkanol in alkaline solution and dimethyl sulfoxide as solvent (q.v. "The Chemistry of the Hydroxyl Group", pp. 83–124; Interscience Publishers Inc., New York, 1971).

Benzoylisocyanates of formula III can be obtained, inter alia, as follows (q.v. J. Agr. Food Chem. 21, 348 and 993; 1973):

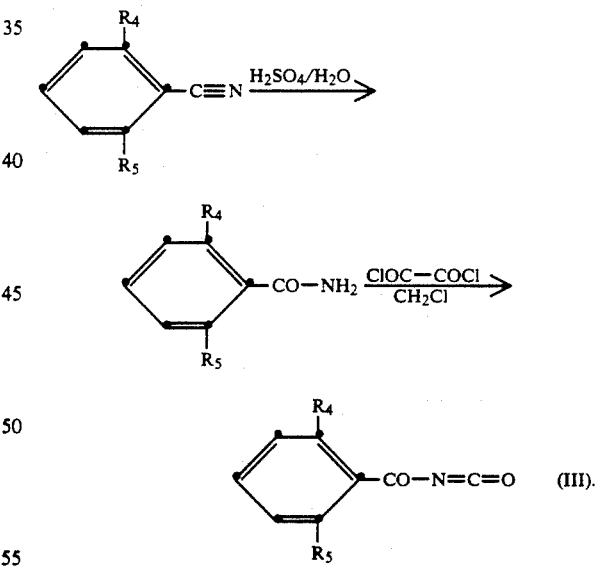

The 4-haloalkoxyphenylisocyanates of formula IV can be prepared e.g. by phosgenating the anilines of formula II by methods which are commonly employed in the art. The benzamides of formula V which are further used as starting materials are known (q.v. for example Beilstein "Handbuch der organischen Chemie", Vol. 9, p. 336).

Urethanes of formula VI can be obtained in a manner known per se by reacting a benzoylisocyanate of formula III with a suitable alcohol or by reacting a benzamide of formula V, in the presence of a base, with a corresponding ester of chloroformic acid Cl—COOR.

Surprisingly, it has been found that the compounds of this invention are valuable pesticides while being well tolerated by warm-blooded animals and plants. The compounds of formula I are therefore suitable e.g. for controlling pests on animals and plants. Such pests belong principally to the phylum of Arthropoda, such as in particular insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera and of arachnids of the order Acarina, e.g. mites and ticks. Every development stage of the pests can be controlled, i.e. the adults, pupae and nymphs, and also in particular the larvae and eggs. It is thus possible to control effectively in particular larvae and eggs of phytopathogenic insect pests and mites in crops of ornamentals and useful plants, e.g. in fruit and vegetable crops, and especially in cotton crops. If compounds of formula I are ingested by imagines, then a direct kill of the pests or a reduced oviposition and/or hatching rate can be observed. This last activity can be observed in particular in Coleoptera. In the control of pests that are parasites of animals, in particular of domestic animals and productive livestock, the compounds of the invention are suitable above all against ectoparasites, e.g. mites and ticks and Diptera such as Lucilia sericata.

The good pesticidal activity of the compounds of formula I of the invention corresponds to a mortality of at least 50–60% of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbons atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids.

These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients in order to obtain special effects.

EXAMPLE 1: PREPARATION 1.1. Intermediates 1.1.1. Nitrobenzenes 1.1.1.1.

2-Fluoro-4-(2,2,2-trifluoroethoxy)-5-chloronitrobenzene 22.5 g of 88% potassium hydroxide are suspended in 120 ml of dimethyl sulfoxide. With stirring, 40 g of trifluoroethanol are added dropwise to this suspension. Then, also with stirring, the resultant solution is added dropwise at room temperature to a solution of 96.8 g of 2,4-difluoro-5-chloronitrobenzene in 150 ml of dimethyl sulfoxide. When the addition is complete, the reaction mixture is stirred for a further 2 hours at room temperature. The reaction mixture is then concentrated, the crude product is dissolved in methylene chloride, and the resultant solution is washed with water and dried. Finally, the solvent is distilled off. Purification is effected by chromatography through a column of silica gel with a 10:1 mixture of hexane and ether as eluant. The solvent is distilled off, affording the title compound of the formula

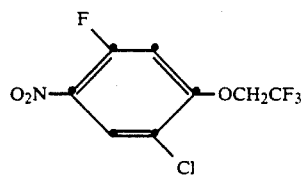

(Compound 1.1.1.1.)

in the form of yellow crystals; m.p.: 54°–55° C.

The following compounds are prepared in analogous manner:

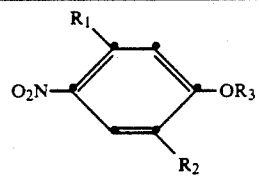

| Compound | $R_1$ | $R_2$ | $R_3$ | Physical data |
|---|---|---|---|---|
| 1.1.1.2. | F | Cl | CH(CF$_3$)$_2$ | $n_D^{23}$: 1.4564 |
| 1.1.1.3. | F | F | CH$_2$CF$_3$ | b.p. 95° C./0.01 torr |
| 1.1.1.4 | F | F | CH$_2$CF$_2$CF$_3$ | b.p. 108° C./0.01 torr |
| 1.1.1.5. | F | Cl | CH$_2$(CF$_2$)$_2$CF$_3$ | $n_D^{23}$: 1.4686 |

1.1.2. Anilines 1.1.2.1.

2-Fluoro-4-(2,2,2-trifluoroethoxy)-5-chloroaniline 21.3 g of the above nitrobenzene are dissolved in 220 ml of tetrahydrofuran and hydrogenated at room temperature for 19 hours in the presence of 4 g of Raney nickel (H$_2$ uptake: 5.26 l). The reaction mixture is filtered, the solvent is distilled off, and the residue is distilled. The title compound of the formula

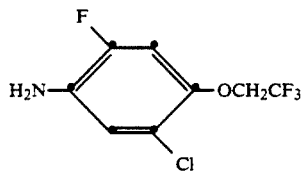

(Compound 1.1.2.1.)

has a boiling point of 166° C./0.08 torr and a melting point of 40°–41° C.

The following compounds are prepared in analogous manner:

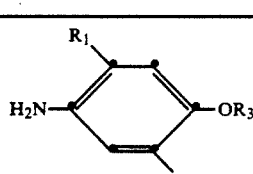

| Compound | $R_1$ | $R_2$ | $R_3$ | Physical data |
|---|---|---|---|---|
| 1.1.2.2. | F | Cl | CH(CF$_3$)$_2$ | m.p. 74–75° C. |
| 1.1.2.3. | F | Cl | CH$_2$(CF$_2$)$_2$CF$_3$ | b.p. 120° C./0.05 torr |
| 1.1.2.4. | F | F | CH$_2$CF$_3$ | b.p. 80° C./0.01 torr |
| 1.1.2.5. | F | F | CH$_2$CF$_2$CF$_3$ | b.p. 83° C./0.01 torr |

1.1.2.6.
2-Fluoro-(4-1,1,2,3,3,3-hexafluoropropoxy)-5-bromoaniline 28 g of 2-bromo-4-amino-5-fluorophenol and 1.9 ml of triethylamine are charged into 150 ml of dimethylformamide. 22.5 g of hexafluoropropylene are then introduced at room temperature, whereupon the temperature of the batch rises to 50° C. The solvent is subsequently distilled off in vacuo, the residue is taken up in ether, and the ethereal solution is extracted twice with dilute sodium hydroxide solution and twice with water. The ethereal extract is dried over sodium sulfate and then subjected to fractional distillation, affording the title compound of the formula

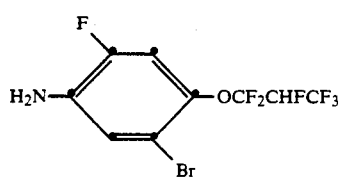

(Compound 1.1.2.6.)

in the form of a pale yellow liquid; b.p.: 76°–81° C./0.001 torr.

The following compounds are prepared in analogous manner:

| Compound | $R_1$ | $R_2$ | $R_3$ | Physical data |
|---|---|---|---|---|
| 1.1.2.7. | F | Cl | $CF_2CHFCF_3$ | b.p. 74–76° C./0.01 torr |
| 1.1.2.8. | F | F | $CF_2CHFCF_3$ | b.p. 56–58° C./0.15 torr |
| 1.1.2.9. | F | Cl | $CF_2CHFCF(CF_3)_2$ | b.p. 150° C./0.04 torr |

1.2. Final product
1.2.1.
N-(2,6-Difluorobenzoyl)-N'-[2-fluoro-4-(2,2,2-trifluoroethoxy)-5-chlorophenyl]urea A solution of 3.0 g of 2,6-difluorobenzoylisocyanate in 10 ml of dry toluene is added at room temperature to a solution of 4 g of 2-fluoro-4-(2,2,2-trifluoroethoxy)-5-chloroaniline in 50 ml of dry toluene, and the batch is stirred for 10 hours. Subsequently, about 75% of the solvent is removed by rotary evaporation. The resultant precipitate is isolated by suction filtration, washed with a small amount of cold toluene and hexane and dried in vacuo, affording the title compound of the formula

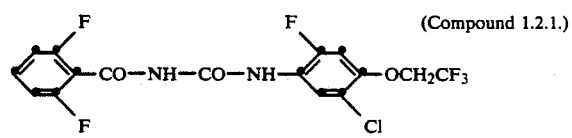

(Compound 1.2.1.)

in the form of a white, crystalline powder; m.p.: 201°–202° C.

The following compounds are prepared in analogous manner:

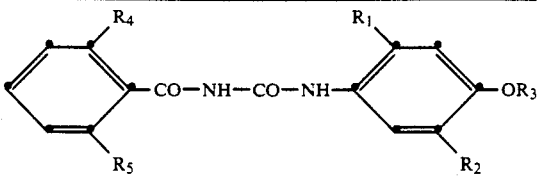

| Compound | $R_1$ | $R_2$ | $R_3$ | $R_4$ | $R_5$ | m.p. °C. |
|---|---|---|---|---|---|---|
| 1.2.2. | F | Cl | $CH_2CF_3$ | H | Cl | 184–186 |
| 1.2.3. | F | Cl | $CH_2CF_3$ | H | F | 184–185 |
| 1.2.4. | F | Cl | $CH_2CF_3$ | F | Cl | 225–227 |
| 1.2.5. | F | Cl | $CH(CF_3)_2$ | H | Cl | 220–221 |
| 1.2.6. | F | Cl | $CH(CF_3)_2$ | F | F | 253–254 |
| 1.2.7. | F | Cl | $CH(CF_3)_2$ | H | F | 218–219 |
| 1.2.8. | F | Cl | $CH(CF_3)_2$ | Cl | Cl | 222–223 |
| 1.2.9. | F | Cl | $CH(CF_3)_2$ | F | Cl | 241–243 |
| 1.2.10. | F | Cl | $CH(CF_3)_2$ | F | $OCH_3$ | 110–111 |
| 1.2.11. | F | Cl | $CF_2CHFCF_3$ | F | F | 163–164 |
| 1.2.12. | F | Cl | $CF_2CHFCF_3$ | H | Cl | 138–140 |
| 1.2.13. | F | F | $CH_2CF_2CF_3$ | F | F | 170–172 |
| 1.2.14. | F | F | $CH_2CF_2CF_3$ | H | Cl | 169–170 |
| 1.2.15. | F | F | $CH_2CF_3$ | F | F | 177–178 |
| 1.2.16. | F | Cl | $CH_2(CF_2)_2CF_3$ | H | Cl | 136–138 |
| 1.2.17. | F | Cl | $CH_2(CF_2)_2CF_3$ | F | F | 182–185 |
| 1.2.18. | F | Cl | $CF_2CHFCF(CF_3)_2$ | F | F | 158–162 |
| 1.2.19. | F | Br | $CF_2CHFCF_3$ | F | F | 159–161 |
| 1.2.20. | F | Br | $CF_2CHFCF_3$ | H | Cl | 142–143 |
| 1.2.21. | F | Br | $CF_2CHFCF_3$ | H | F | 139–140 |
| 1.2.22. | F | Br | $CF_2CHFCF_3$ | F | Cl | 190–192 |
| 1.2.23. | F | Br | $CF_2CHFCF_3$ | F | $OCH_3$ | 172–174 |
| 1.2.24. | F | F | $CF_2CHFCF_3$ | F | F | 165–166 |
| 1.2.25. | F | F | $CF_2CHFCF_3$ | H | Cl | 169–170 |
| 1.2.26. | F | F | $CF_2CHFCF_3$ | H | F | 163–164 |
| 1.2.27. | F | F | $CF_2CHFCF_3$ | F | Cl | 191–193 |
| 1.2.28. | F | Cl | $CF_2CHFCF_3$ | H | F | 135–136 |
| 1.2.29. | F | Cl | $CF_2CHFCF_3$ | F | Cl | 198–199 |
| 1.2.30. | F | Cl | $CF_2CHFCF_3$ | Cl | Cl | 184–185 |
| 1.2.31. | F | Cl | $CF_2CHFCF_3$ | F | $OCH_3$ | 172–173 |
| 1.2.32. | F | Cl | $CF_2CHFCF_3$ | H | $OCH_3$ | 162–163,5 |
| 1.2.33. | F | Cl | $CF_2CHFCF_3$ | $OCH_3$ | $OCH_3$ | 175–177 |
| 1.2.34. | F | Br | $CF_2CHFCF_3$ | Cl | Cl | 181–182 |
| 1.2.35. | F | Br | $CF_2CHFCF_3$ | H | $OCH_3$ | 159–161 |
| 1.2.36. | F | Br | $CF_2CHFCF_3$ | $OCH_3$ | $OCH_3$ | 184–185 |
| 1.2.37. | F | F | $CF_2CHFCF_3$ | Cl | Cl | |
| 1.2.38. | F | F | $CF_2CHFCF_3$ | F | $OCH_3$ | |
| 1.2.39. | F | F | $CF_2CHFCF_3$ | H | $OCH_3$ | |
| 1.2.40. | F | F | $CF_2CHFCF_3$ | $OCH_3$ | $OCH_3$ | |

EXAMPLE 2

Formulation Examples for active ingredients of formula I according to Preparatory Example 1.2 (throughout, percentages are by weight)

| 2.1. Emulsifiable concentrates | (a) | (b) |
|---|---|---|
| a compound according to Preparatory Example 1.2 | 10% | 25% |
| calcium dodecylbenzenesulfonate | — | 5% |
| castor oil polyethylene glycol ether (36 moles of ethylene oxide) | — | 5% |
| tributylphenol polyethylene glycol ether (30 moles of ethylene oxide) | — | — |
| castor oil thioxilate | 25% | — |
| cyclohexanone | — | — |
| butanol | 15% | — |
| xylene mixture | — | 65% |
| ethyl acetate | 50% | — |

Emulsions of any required concentration can be produced from such concentrates by dilution with water.

| 2.2. Solutions | (a) | (b) |
|---|---|---|
| a compound according to Preparatory Example 1.2 | 10% | 5% |
| ethylene glycol monomethyl ether | — | — |
| polyethylene glycol 400 | 70% | — |
| N-methyl-2-pyrrolidone | 20% | 20% |
| epoxidised coconut oil | — | 1% |
| petroleum distillate (boiling range 160–190° C.) | — | 74% |

These solutions are suitable for application in the form of microdrops.

| 2.3. Granulates | (a) | (b) |
|---|---|---|
| a compound according to Preparatory Example 1.2 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Extruder granulate | |
|---|---|
| a compound according to Preparatory Example 1.2 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.5. Coated granulate | |
|---|---|
| a compound according to Preparatory Example 1.2 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 2.6. Dusts | (a) | (b) | (c) | (d) |
|---|---|---|---|---|
| a compound according to Preparatory Example 1.2 | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient.

| 2.7. Wettable powders | (a) | (b) | (c) |
|---|---|---|---|
| a compound according to Preparatory Example 1.2 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.8. Suspension concentrate | |
|---|---|
| a compound according to Preparatory Example 1.2 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3: Biological Tests 3.1. Action against *Musca domestica*

50 g of freshly prepared CSMA nutrient substrate for maggots are charged into a beaker. 5 ml of an acetonic solution containing 1% by weight of the test compound is pipetted onto the nutrient substrate present in the beaker. The substrate is then thoroughly mixed and the acetone subsequently allowed to evaporate over a period of at least 20 hours.

Then 25 one-day-old maggots of *Musca domestica* are put into the beaker containing the treated nutrient substrate. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds according to Example 1.2 exhibit good activity in this test.

3.2. Action against *Lucilia sericata*

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds according to Example 1.2 exhibit good activity against *Lucilia sericata*.

3.3. Action against *Aëdes aegypti*

A concentration of 12.5 ppm is obtained by pipetting a specific amount of a 0.1% solution of the test compound in acetone onto the surface of 150 ml of water in a beaker. After the acetone has evaporated, 30 to 40 two-day-old larvae of *Aëdes aegypti* are put into the beaker containing the test compound. Mortality counts are made after 2 and 7 days.

Compounds according to Example 1.2 exhibit good activity in this test.

3.4. Insecticidal Action Against Feeding Insects

Cotton plants (about 20 cm high) are sprayed with an aqueous emulsion (obtained from a 10% emulsifiable concentrate) containing 100 ppm of the test compound. After the spray coating has dried, the cotton plants are populated with *Spodoptera littoralis* and *Heliothis virescens* larvae in the $L_3$-stage. The test is carried out at 24° C. and 60% relative humidity. At 24 hour intervals, a mortality count is made and the larvae are also examined for inhibition of development and moulting.

Compounds according to Example 1.2 exhibit good activity in this test.

3.5. Action against *Spodoptera littoralis* and *Heliothis virescens* (larvae and eggs)

Three cotton plants each having a height of about 15-20 cm and grown in pots are treated with a sprayable liquid preparation of the test compound. After the spray coating has dried, the potted plants are placed in a metal container having a capacity of about 20 liters and covered with a glass plate. The humidity in the interior of covered container is regulated such that no water of condensation forms. Direct light falling on the plants is avoided. The three plants are then infested altogether with:
a) 50 larvae of *Spodoptera littoralis* or *Heliothis virescens* in the $L_1$-stage;
b) 20 larvae of *Spodoptera littoralis* or *Heliothis virescens* in the $L_3$-stage;
c) 2 eggs deposits of *Spodoptera littoralis* or *Heliothis virescens*. (The procedure is that two leaves of each plant are put into a plexiglass cylinder sealed at both ends with gauze. Two egg deposits of Spodoptera, or a part of a cotton leaf with eggs of Heliothis deposited thereon, are added to the leaves sealed in the cylinder.)

Evaluation in comparison with untreated controls is made after 4 to 5 days, taking into account the following criteria:
a) the number of still living larvae,
b) inhibition of larval development and moulting,
c) feeding damage (shredding and perforation damage),
d) hatching rate (number of larvae hatched from the eggs).

In this test, compounds according to Example 1.2 exhibit good overall activity at a concentration of 400 ppm.

3.6. Ovicidal action against *Spodoptera littoralis*

Eggs of *Spodoptera littoralis* deposited on filter paper are cut out of the paper and immersed in a 0.05% by weight solution of the test compound in a 1:1 mixture of acetone-water. The treated deposits are then removed from this mixture and kept in plastic dishes at 28° C. and 60% humidity. The hatching rate, i.e. the number of larvae which have developed from the treated eggs, is determined after 5 days.

Compounds according to Example 1.2 show good activity in this test.

3.7. Action against *Laspeyresia pomonella* (eggs)

Eggs deposits of *Laspeyresia pomonella* not more than 24 hours old are immersed on filter paper for 1 minute in an aqueous acetonic solution containing 400 ppm of the test compound.

After the solution has dried, the filter paper and the eggs are placed in petri dishes and kept at a temperature of 28° C. The percentage of larvae hatched from the treated eggs is evaluated after 6 days.

Compounds according to Example 1.2 exhibit good activity in this test.

3.8. Influence on the reproduction of *Anthonomus grandis*

Anthonomus grandis adults which are not more than 24 hours old after hatching are transferred in groups of 25 to barred cages. The cages are then immersed for 5 to 10 seconds in an acetonic solution containing 0.1% by weight of the test compound. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine whether larvae have developed from the eggs.

The duration of the reproduction inhibiting effect of the test compounds is determined by monitoring the egg deposits over a period of about 4 weeks. Evaluation is made by assessing the reduction in the number of deposited eggs and hatched larvae in comparison with untreated controls.

Compounds according to Example 1.2 exhibit a good reproduction inhibiting effect in this test.

3.9. Action against *Anthonomus grandis* (adults)

Two cotton plants in the 6-leaf stage, in pots, are each sprayed with a wettable aqueous emulsion formulation containing 100 ppm of the test compound. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Compounds according to Example 1.2 exhibit good activity in this test.

3.10: Action against *Epilachna varivestis*

Phaseolus vulgaris plants (dwarf beans) about 15-20 cm in height are sprayed with aqueous emulsion formulations of the test compound in a concentration of 800 ppm. After the spray coating has dried, each plant is populated with 5 larvae of *Epilachna varivestis* (Mexican bean beetle) in the $L_4$-stage. A plastic cylinder is slipped over the treated plants and covered with a copper gauze top. The test is carried out at 28° C. and 60% relative humidity. The percentage mortality is determined after 2 and 3 days. Evaluation of feeding damage (anti-feeding effect), and of inhibition of development and shedding, is made by observing the test insects for a further 3 days.

Compounds according to Example 1.2 exhibit good activity in this test.

3.11: Ovicidal action against *Heliothis virescens* and *Spodoptera littoralis*

Corresponding amounts of a wettable powder formulation containing 25% by weight of the test compound are mixed with sufficient water to produce an aqueous emulsion with an active ingredient concentration of 400 ppm. One-day-old egg deposits of Heliothis on cellophane and of Spodoptera on paper are immersed in these emulsions for 3 minutes and then collected by suction on round filters. The treated deposits are placed in petri dishes and kept in the dark at 28° C. and 60% relative humidity. The hatching rate, i.e. the number of larvae which have developed from the treated eggs, in comparison with untreated controls is determined after 5 to 8 days.

Compounds according to Example 1.2 exhibit an 80 to 100% ovicidal activity (mortality) in this test.

3.12 Action against *Laspeyresia pomonella* (eggs)

Egg deposits of *Laspeyresia pomonella* not more than 24 hours old are immersed on filter paper for 1 minute in an aqueous acetonic solution containing 800 ppm of the test compound.

After the solution has dried, the eggs are placed in petri dishes and kept at a temperature of 28° C. The percentage of larvae hatched from the treated eggs and the percentage mortality is evaluated after 6 days.

Compounds according to Example 1.2 exhibit good activity in this test.

What is claimed is:

1. A compound of formula I

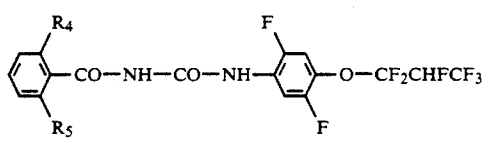

wherein $R_4$ is hydrogen, chlorine, fluorine or methoxy and $R_5$ is chlorine, fluorine or methoxy.

2. A compound of formula I according to claim 1, wherein $R_4$ is hydrogen, fluorine or chlorine and $R_5$ is fluorine, chlorine or methoxy.

3. The compound according to claim 1 of the formula

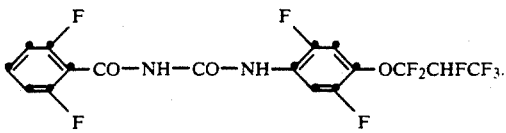

4. The compound according to claim 1 of the formula

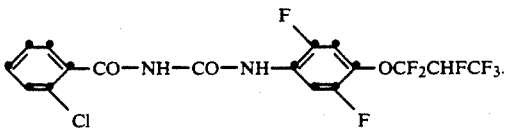

5. The compound according to claim 1 of the formula

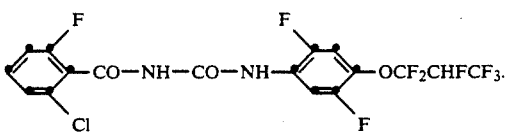

6. A pesticidal composition which contains, as active ingredient, at least one compound of formula I

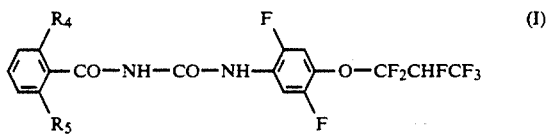

wherein $R_4$ is hydrogen, chlorine, fluorine or methoxy and $R_5$ is chlorine, fluorine or methoxy, and a carrier.

7. A pesticidal composition according to claim 6, wherein $R_4$ is hydrogen, fluorine or chlorine and $R_5$ is fluorine, chlorine or methoxy.

* * * * *